US009023761B2

(12) United States Patent
Goren et al.

(10) Patent No.: US 9,023,761 B2
(45) Date of Patent: May 5, 2015

(54) COMPOSITIONS AND METHODS FOR BLOCKING ETHYLENE RESPONSE IN PLANTS USING 3-CYCLOPROPYL-1-ENYL-PROPANOIC ACID SALT

(75) Inventors: Raffi Goren, Rehovot (IL); Akiva Apelbaum, Rehovot (IL); Eliezer Goldschmidt, Rehovot (IL); Moshe Huberman, Rehovot (IL); Joseph Riov, Petach Tikva (IL); Edward C. Sisler, Raleigh, NC (US)

(73) Assignees: Yissum Research Development Company of the Hebrew University of Jerusalem Ltd., Jerusalem (IL); North Carolina State University, Raleigh, NC (US)

( * ) Notice: Subject to any disclaimer, the term of this patent is extended or adjusted under 35 U.S.C. 154(b) by 1219 days.

(21) Appl. No.: 12/669,600

(22) PCT Filed: Jul. 17, 2008

(86) PCT No.: PCT/IL2008/000995
§ 371 (c)(1),
(2), (4) Date: Jul. 13, 2011

(87) PCT Pub. No.: WO2009/010981
PCT Pub. Date: Jan. 22, 2009

(65) Prior Publication Data
US 2012/0004106 A1 Jan. 5, 2012

(30) Foreign Application Priority Data

Jul. 19, 2007 (IL) .......................................... 184729

(51) Int. Cl.
| | | |
|---|---|---|
| A01N 3/00 | (2006.01) | |
| A01N 3/02 | (2006.01) | |
| A01N 53/00 | (2006.01) | |
| A01N 37/08 | (2006.01) | |
| A01N 37/06 | (2006.01) | |
| A23B 7/154 | (2006.01) | |

(52) U.S. Cl.
CPC .. A01N 3/00 (2013.01); A01N 3/02 (2013.01); A01N 37/06 (2013.01); A23B 7/154 (2013.01)

(58) Field of Classification Search
USPC ............ 504/114, 320; 562/506, 510; 514/572
See application file for complete search history.

(56) References Cited

U.S. PATENT DOCUMENTS

| | | | |
|---|---|---|---|
| 3,879,188 A | 4/1975 | Fritz et al. | |
| 5,510,315 A | 4/1996 | Kurotsu et al. | |
| 5,518,988 A | 5/1996 | Sisler et al. | |
| 5,679,617 A | 10/1997 | Hanafusa et al. | |
| 5,834,403 A | 11/1998 | Callan | |
| 6,194,350 B1 | 2/2001 | Sisler | |
| 6,365,549 B2 | 4/2002 | Sisler | |
| 7,041,625 B2 | 5/2006 | Jacobson et al. | |
| 8,093,430 B2 | 1/2012 | Sisler | |
| 8,329,954 B2 | 12/2012 | Sisler | |

FOREIGN PATENT DOCUMENTS

| | | |
|---|---|---|
| CN | 1450859 | 10/2003 |
| CN | 1505933 | 6/2004 |
| JP | 2003-533972 | 11/2003 |
| WO | WO 01/37663 | 5/2001 |
| WO | WO 01/37663 A2 | 5/2001 |
| WO | WO 02/068367 | 9/2002 |
| WO | WO 2009/010981 | 1/2009 |

OTHER PUBLICATIONS

Goren, R., et al., "Effect of 3-cyclopropyl-1-enyl-propanoic acid sodium salt, a novel water soluble antagonist of ethylene action, on plant responses to ethylene," Plant Growth Regul 65:327-334, Springer Science+Business Media B.V., Netherlands (2011).
Grichko, V., "New Volatile and Water-Soluble Ethylene Antagonists," Russian Journal of Plant Physiology 53(4):523-529, Nauka/Interperiodica, Russia (2006).
Sisler, E.C., et al., "The effect of dialkylamine compounds and related derivatives of 1-methylcyclopropene in counteracting ethylene responses in banana fruit," Postharvest Biology and Technology 51:43-48, Elsevier B.V., Netherlands (2009).
International Preliminary Report on Patentability for International Application No. PCT/IL2008/000995, European Patent Office, Germany, completed on Oct. 8, 2009.
International Search Report for International Application No. PCT/IL2008/000995, European Patent Office, Netherlands, mailed on Nov. 6, 2008.
Substantive Examination Report and Search Report Dated Jun. 11, 2012 From the African Regional Intellectual Property Organization (ARIPO) Re. Application No. AP/P/2010/005165.
Translation of Office Action Dated Jun. 21, 2013 From the State Intellectual Property Office of the People's Republic of China Re. Application No. 200880024068.6.
Communication Pursuant to Article 94(3) EPC Dated Aug. 23, 2010 From the European Patent Office Re. Application No. 08776627.5.
International Preliminary Report on Patentability Dated Oct. 8, 2009 From the International Preliminary Examining Authority Re. Application No. PCT/IL2008/000995.
International Search Report and the Written Opinion Dated Nov. 6, 2008 From the International Searching Authority Re. Application No. PCT/IL2008/000995.
Translation of Office Action Dated Oct. 8, 2012 From the State Intellectual Property Office of the People's Republic of China Re. Application No. 200880024068.6.
Translation of Search Report Dated Oct. 8, 2012 From the State Intellectual Property Office of the People's Republic of China Re. Application No. 200880024068.6.

(Continued)

Primary Examiner — John Pak
Assistant Examiner — Andriae M Holt

(57) ABSTRACT

The present invention discloses a method of inhibiting an ethylene response in a plant, comprising step of applying to at least one portion of the plant an effective ethylene response-inhibiting amount of a H1-cyclopropene-1-propanoic acid salt (CPAS). A method of prolonging the life of a cut flower, comprising applying to the cut flower an effective life-prolonging amount of CPAS and a method for the production a CPAS, comprising steps of (i) preparing 4-bromo-4-pentenoic acid or derivatives thereof; (ii) producing 1-cyclopropene-1-propanoic acid; and (iii) converting this acid into its water soluble salt, especially its sodium salt are presented. Additionally, a new family of water soluble CPAS inhibitors for ethylene response in a plant is disclosed.

29 Claims, 27 Drawing Sheets

(56) References Cited

OTHER PUBLICATIONS

Grichko "New Volatile and Water-Soluble Ethylene Antagonists", Russian Journal of Plant Physiology, XP019407768, 53(4): 523-529, Jul. 1, 2006. p. 523, col. 2, Para 1-2 From the Bottom, p. 523, r-h Col., Para 2-p. 524, r-h Col., Para 1, p. 524, col. 1, Para 1, p. 524, col. 2, Last Line, p. 526, Table 1, XI, XII, Compounds XI, XII, p. 527, col. 1, Lines 1-2, p. 527, Table 2, Compounds XI-XII.

Jacobson et al. Corresponding Document: WO 02/068367. Claims 1-9.

Patent Examination Report Dated Jan. 9, 2013 From the Australian Government, IP Australia Re. Application No. 2008277270.

Summons to Attend Oral Proceedings Pursuant to Rule 115(1) EPC Dated Mar. 21, 2014 From the European Patent Office Re. Application No. 08776627.5.

Office Action Dated Mar. 12, 2014 From the State Intellectual Property Office of the People's Republic of China Re. Application No. 200880024068.6 and Its Translation Into English.

Requisition by the Examiner Dated Nov. 21, 2013 From the Canadian Intellectual Property Office Re. Application No. 2,693,971.

Office Action Dated Dec. 24, 2013 From the Israel Patent Office Re. Application No. 203370 and Its Translation Into English.

Conclusion on Patentability of Invention Dated Mar. 4, 2013 From the Eurasian Patent Organization, The Eurasian Patent Office Re. Application No. 201070032 and Its Translation Into English.

Notice of Final Rejection Dated Apr. 16, 2013 From the Japanese Patent Office Re. Application No. 2010-516652 and Its Translation Into English.

Notice of Reasons for Rejection Dated Dec. 11, 2012 From the Japanese Patent Office Re. Application No. 2010-516652 and Its Translation Into English.

Notification on Necessity of Presenting Additional Materials Dated Jun. 27, 2012 From the Eurasian Patent Organization, The Eurasian Patent Office Re. Application No. 201070032 and Its Translation Into English.

Substantial Examination Report Dated Feb. 12, 2013 From the Superindencia de Industria y Comercio of the Colombian Patent Office (CPO) Re. Application No. 10-19208 and Its Translation Into English.

Examination Report Dated Jul. 16, 2014 From the Government of India, Patent Office, Intellectual Property Building Re. Application No. 88/MUMNP/2010.

Office Action Dated Jul. 6, 2014 From the Israel Patent Office Re. Application No. 203370 and Its Translation Into English.

The Minutes in Accordance With Rule 124(4) EPC Dated Nov. 12, 2014 From the European Patent Office Re. Application No. 08776627.5.

Al Dulayymi et al. "1,2,2-Tribromocyclopropanecarboxylic Acid and Derivation—Valuable Intermediates for Four Carbon Cyclopropane and Cyclopropene Synthons", Tetrahedron, 52(10): 3409-3424, 1996.

Al Dulayymi et al. "Structure Based Interference With Insect Behaviour—Cyclopropene Analogues of Pheromones Containing Z-Alkenes", Tetrahedron, 52(38): 12509-12520, 1996.

A

A

B

A            B

A       B

A

B

CERTIFICATE OF ANALYSIS

| Product Brand Name: | Agri-2 |
|---|---|
| Product Chemical Name: | 3-(1-Cyclopropenyl)propanoic acid, sodium salt |
| Batch number: | R-898 (lab. Notebook 510, p.79) |
| Quantity | 8 vials x 250mg each |
| Manufacturer | D-Pharm Ltd, Israel |

| Name of Test | Test Results |
|---|---|
| Appearance: | White powder |
| Identification: NMR MS | 1H-NMR spectral data correspond to the structure of the compound. MS (ESI): m/z 110.9 correspond to $C_6H_7O_2^-$ |
| Chromatographic purity (HPLC): | 91.16% (RT: 13.48 min) |
| Sodium content: | 98.4% (potentiometric titration) |
| Main impurity | 3.89% (RT 14.73 min), 2.69 (RT 14.56min) |

Store at ca. -18 °C, tightly closed. Open only after reaching room temperature
Protect from light and humidity.
Transport is permitted at temperature of dry ice.
Test records: lab notebook 526, p102; lab notebook 536, p.18

Director, Chemical & Analytical R&D:     Dr Israel Shapiro

FIG. 26A

CERTIFICATE OF ANALYSIS

| Product Brand Name: | Agri-2 |
|---|---|
| Product Chemical Name: | 3-(1-Cyclopropenyl)propanoic acid, sodium salt |
| Batch number: | R-905 (lab. Notebook 510, p.72) |
| Quantity | 22 vials x 250mg each, 1vial x 160mg |
| Manufacturer | D-Pharm Ltd, Israel |

| Name of Test | Test Results |
|---|---|
| Appearance: | White powder |
| Identification: NMR MS | 1H-NMR spectral data correspond to the structure of the compound. MS (ESI): m/z 110.9 correspond to $C_6H_7O_2^-$ |
| Chromatographic purity (HPLC): | 89% (RT: 13.7 min) |
| Sodium content: | 93.6% (potentiometric titration) |
| Main impurity | 7.1% (RT 14.76 min) |

Store at ca. -18 °C, tightly closed. Open only after reaching room temperature
Protect from light and humidity.
Transport is permitted at temperature of dry ice
Test records: lab notebook 526, p113; lab notebook 536, p.29

Director, Chemical & Analytical R&D:   Dr Israel Shapiro

FIG. 26B

COMPOSITIONS AND METHODS FOR BLOCKING ETHYLENE RESPONSE IN PLANTS USING 3-CYCLOPROPYL-1-ENYL-PROPANOIC ACID SALT

FIELD OF THE INVENTION

The present invention generally relates to water soluble compositions and methods of blocking ethylene responses in plants and plant organs or tissues, and particularly relates to methods of inhibiting various ethylene controlled vegetative, regenerative and reproductive processes in plants by applying 3-cyclopropyl-1-enyl-propanoic acid sodium (or other positively charged counter ions) salt (CPAS) to plants. The invention also pertains to a method of CPAS synthesis.

BACKGROUND OF THE INVENTION

Ethylene is a natural plant growth regulator involved in numerous developmental processes, in particular fruit ripening, abscission (fruit and leaf drop), and senescence. Adverse effects of ethylene harm agricultural output.

Antagonists of ethylene action are considered very beneficial for agricultural use, since they protect the tissues from both endogenous and exogenous ethylene. Ethylene antagonists (EAs) inhibit the action of ethylene at the molecular level by blocking its receptor site. Thus, application of EAs may allow extending harvest season of crops, prolonging storability and shelf life of fruit, herbs and leafy vegetables, and extending the vase life of cut flowers. Use of some EAs has been protected by patents: phosphonic acid derivatives (U.S. Pat. No. 3,879,188), silver thiosulphate (U.S. Pat. No. 5,510,315), organohalogen compounds (U.S. Pat. No. 5,679,617), 2,5-norbornadiene (U.S. Pat. No. 5,834,403), 1-methylcyclopropene (U.S. Pat. No. 619,350, U.S. Pat. No. 6,365,549).

Notwithstanding the progress in methods of blocking ethylene response, there is still felt need for safe and convenient water soluble blocking agents.

SUMMARY OF THE INVENTION

The use of the most promising antagonist of ethylene presently available, 1-methylcyclopropene (1-MCP), is limited mainly due to its insolubility in water and therefore, is used in a volatile form only in sealed chambers. It cannot be used for dip loading of cut flowers or application as a spray in the field. In addition, a greater selection of ethylene antagonist is commercially desired to meat the marked demand for inhibitors that block the ethylene receptor for various lengths of time. Seventeen cyclopropene putative inhibitors of ethylene action were synthesized and screened for their potency as ethylene antagonists. The most promising one was selected in order to further synthesize the novel water and stable cyclopropene derivative (CPAS) that was found to be an effective inhibitor of ethylene-induced adverse responses in agricultural crops, like delaying banana peel de-greening at least by 12 days, and color change of 'Hass' avocado fruit at least by 5 days, prolonging the vase-life of carnation and petunia cut flowers at least by 14 days, as well as delaying abscission of citrus leaf explants at least by 7 days.

Methods of inhibiting ethylene responses in plants are hence disclosed herein. According to the present invention, one such method comprises applying to the plant an effective ethylene response-inhibiting amount of CPAS described further in detail.

Another aspect of the present invention is a method of blocking ethylene receptors in plants by applying to the plants an effective ethylene receptor-blocking amount of CPAS.

Another aspect of the present invention is a method of blocking ethylene receptors in plants by the method as defined above, wherein the method additionally comprising a step of admixing the CPAS with an effective measure of a surfactant, such surface-active CPAS-containing aqueous solution is obtained.

Also disclosed is a method of inhibiting abscission in a plant, comprising applying to the plant an effective abscission-inhibiting amount of CPAS.

Also disclosed is a method of prolonging the life of a cut flower, comprising applying to the cut flower an effective life-prolonging amount of CPAS.

Also disclosed is a method of inhibiting the ripening of a harvested fruit, comprising applying to the harvested fruit an effective inhibiting amount of CPAS. Also disclosed is a method of inhibiting the ripening of a harvested vegetable, comprising applying to the harvested vegetable an effective inhibiting amount of CPAS. The methods described herein may be carried out in a number of suitable manners, such as by treating the plant with CPAS, whether (i) in aqueous solution, or aerosol, or suspension, or emulsion; (ii) or by introducing the plant, cut flower, picked fruit or picked vegetable into an atmosphere containing CPAS aqueous solution; or (iii) in powder, fine-particles e.g., nano-powder, particulate matter, etc. These and other suitable methods of application are discussed in detail below.

It is hence the object of the invention to disclose a method of inhibiting an ethylene response in a plant, comprising applying to at least one portion of the plant an effective ethylene response-inhibiting amount of a cyclopropyl-1-enyl-propanoic acid sodium salt (CPAS), defined by Formula (1):

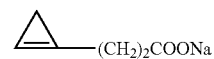

wherein sodium (Na+) is defined hereinafter for any suitable positively charged counter ion.

The applying step is possibly carried out by contacting said compound to an aqueous solution comprising said compound. The CPAS according to the present invention are salts selected in a non-limiting manner from a group of lithium, sodium, potassium, ammonium, calcium, magnesium, etc, and positively charged counter-ions comprising at least one sulfate or phosphate molecules, or a combination thereof, and especially a sodium salt. The applying step is possibly carried out by one or more of the procedures of dipping, spraying, irrigating or drop emitting, contacting, and brushing of at least a part of said plant in the solution. The ethylene response is selected in a non-limiting manner form fruit ripening, vegetable ripening, flower senescence, abscission, harvested fruit, harvested vegetable or a combination of the same.

Another object of the invention is to disclose a method of prolonging the life of a harvested fruit, comprising applying to the cut fruit an effective life-prolonging amount of a compound defined by Formula (1). The applying step is possibly carried out by one or more of the procedures of contacting, dipping, spraying, irrigating or drop emitting, brushing of at least a part of said plant in the solution. The ethylene response is selected in a non-limiting manner form fruit ripening, vegetable ripening, flower senescence, abscission, harvested fruit, harvested vegetable or a combination of the same.

Another object of the invention is to disclose a method of prolonging the life of cut flowers, comprising applying to the cut flower an effective life-prolonging amount of a compound defined by Formula (1). The applying step is possibly carried out by one or more of the procedures of contacting, dipping, spraying, irrigating or drop emitting, brushing of at least a part of said plant in the solution.

Another object of the invention is to disclose a cyclopropyl-1-enyl-propanoic acid sodium salt (CPAS) inhibitor for ethylene response in a plant characterized by Formula (1). The CPAS inhibitor is possibly being dominantly in the liquid form at ambient conditions (temperature and pressure), adapted to be applied on at least a portion of a plant by commercially available means, selected from a group of dipping, brushing, irrigating or drop emitting, spraying or any combination thereof. Alternatively or additionally, the CPAS as defined in any of the above is dissolved, dispersed or admixed in an aqueous solution to an effective measure.

Another object of the invention is to disclose the CPAS as defined above, wherein the CPAS is provided as a surface-active CPAS-containing aqueous solution is obtained.

BRIEF DESCRIPTION OF THE DRAWINGS

This invention will now be described in more detail, by way of examples, with reference to the accompanying drawings in which:

FIG. 26A and FIG. 26B are Certificates of Analysis of synthetically prepared CPAS.

DETAILED DESCRIPTION OF THE INVENTION

Figure 1:
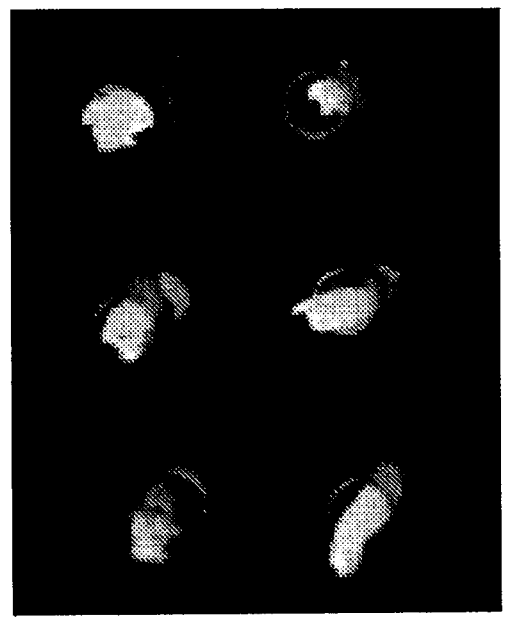
FIG. 1 is a photograph of CPAS-treated and untreated carnation petals.
Figure 1:
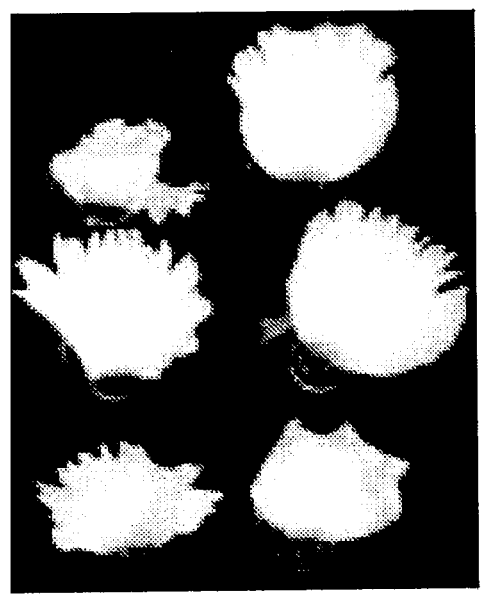

CPAS which may be used to carry out the present invention is defined by Formula I (sodium is provided herein as a positively Charged counter ion).

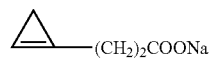

Formula 1

The term "plant" is used in a generic sense herein, and includes herbaceous and woody-stemmed plants such as trees and shrubs. Plants to be treated by the methods described herein include whole plants and any portions thereof, such as field crops, potted plants, cut flowers (stems and flowers), and harvested fruits and vegetables. Plants treated with said compound and by the methods of the present invention are preferably treated with a non-phytotoxic amount of CPAS.

The term 'aqueous solution' refers hereinafter to any at least partially water miscible solution. Notwithstanding with the above, the CPAS is possibly provided in a powder form, as a tablet, an aerosol, emulsion, suspension, water-miscible or water-immiscible solution or in any other agricultural manner.

The present invention can be employed to modify a variety of different ethylene responses. Ethylene responses may be initiated by either exogenous or endogenous sources of ethylene. Ethylene responses include, for example, the ripening and/or senescence of flowers, fruits and vegetables, abscission of foliage, flowers and fruit, the shortening of life of ornamentals such as potted plants, cut flowers, shrubbery, seeds, and dormant seedlings, in some plants (e.g., pea) the inhibition of growth, and in other plants (e.g., rice) the stimulation of growth. Additional ethylene responses or ethylene-type responses that may be inhibited by CPAS of the present invention include, but are not limited to, either direct or indirect auxin activity, inhibition of terminal growth, control of apical dominance, increase in branching, increase or decrease of metabolite product and by-product metabolism and concentration, changing bio-chemical compositions of plants (such as increasing leaf area relative to stem area), abortion or inhibition of flowering and seed development, lodging effects, stimulation of seed germination and breaking of dormancy, and hormone or epinasty effects.

Methods according to embodiments of the present invention inhibit the ripening and/or senescence of vegetables. As used herein, "vegetable ripening" includes the ripening of the vegetable while still on the vegetable-bearing plant and the ripening of the vegetable after having been harvested from the vegetable-bearing plant. Vegetables which may be treated by the method of the present invention to inhibit ripening and/or senescence include leafy green vegetables such as lettuce (e.g., *Lactuea sativa*), spinach (*Spinaca oleracea*), and cabbage (*Brassica oleracea*), various roots, such as potatoes (*Solanum tuberosum*) and carrots (Daucus), bulbs, such as onions (*Allium* sp.), herbs, such as basil (*Ocimum basilicum*), oregano (*Origanum vulgare*), dill (*Anethum graveolens*), as well as soybean (*Glycine max*), lima beans (*Phaseolus limensis*), peas (*Lathyrus* spp.), corn (*Zea mays*), broccoli (*Brassica oleracea italica*), cauliflower (*Brassica oleracea botrytis*), and asparagus (*Asparagus officinalis*).

Methods according to embodiments of the present invention inhibit the ripening of fruits. As used herein, "fruit ripening" includes the ripening of fruit while still on the fruit-bearing plant as well as the ripening of fruit after having been harvested from the fruit-bearing plant. Fruits which may be treated by the method of the present invention to inhibit ripening include tomatoes (*Lycopersicon esculentum*), apples (*Malus domestica*), bananas (*Musa sapientum*), pears (*Pyrus communis*), papaya (*Carica papaya*), mangoes (*Mangifera indica*), peaches (*Prunus persica*), apricots (*Prunus armeniaca*), nectarines (*Prunus persica nectarina*), oranges (*Citrus* sp.), lemons (*Citrus limonia*), limes (*Citrus aurantifolia*), grapefruit (*Citrus paradisi*), tangerines (*Citrus nobilis deliciosa*) and other commercial cultivars, hybrids and new developed cultivars, kiwi (*Actinidia chinenus*), pineapple (*Aranas comosus*), persimmon (*Diospyros* sp.), avocados (*Persea americana*) and other commercial cultivars, hybrids and new developed cultivars.

Ornamental plants which may be treated by the method of the present invention to inhibit senescence and/or to prolong flower life and appearance (e.g., delay yellowing and abscission), include potted ornamentals, and cut flowers. Potted ornamentals and cut flowers which may be treated with the present invention include azalea (*Rhododendron* spp.), hydrangea (*Macrophylla hydrangea*), hybiscus (*Hibiscus rosasanensis*), snapdragons (*Antirrhinum* sp), poinsettia (*Euphorbia pulcherima*), cactus (e.g. *Cactaceae schlumbergera truncata*), begonias (*Begonia* sp.), roses (*Rosa* spp), tulips (*Tulipa* sp.), daffodils (*Narcissus* spp.), petunias (*Petunia hybrida*), carnation (*Dianthus caryophyllus*), lily (e.g., *Minn* sp.), gladiolus (*Gladiolus* sp.), alstroemeria (*Alstoemeria brasiliensis*), anemone (e.g., *Anemone blanda*), columbine (*Aquilegia* sp.), aralia (e.g., *Aralia chinensis*), aster (e.g., *Aster carolinianus*), bougainvillea (*Bougainvillea* sp.), camellia (*Camellia* sp.), bellflower (*Campanula* sp.), cockscomb (*celosia* sp.), falsecypress (*Chamaecyparis* sp.), chrysanthemum (*Chrysanthemum* sp.), clematis (*Clematis* sp.), cyclamen (*Cyclamen* sp.), freesia (e.g., *Freesia refracta*), and orchids of the family Orchidaceae and other commercial cultivars, hybrids and new developed cultivars.

Plants which may be treated by the method of the present invention to inhibit abscission of foliage, flowers and fruit include, apples, pears, cherries (*Prunus avium*), pecans (*Carva illinoensis*), grapes (*Vitis vinifera*), olives (e.g. *Vitis vinifera* and *Olea europaea*), coffee (*Coffea arabica*), snapbeans (*Phaseolus vulgaris*), oranges (*Citrus* sp.), lemons (*Citrus limonia*), limes (*Citrus aurantifolia*), grapefruit (*Citrus paradisi*), tangerines (*Citrus nobilis deliciosa*) and other commercial cultivars, hybrids and new developed cultivars, and weeping fig (*Ficus benjamina*), as well as dormant seedlings such as various fruit trees including apple, ornamental plants, shrubbery, and tree seedlings. In addition, shrubbery which may be treated according to the present invention to inhibit abscission of foliage include privet (*Ligustrum* sp.), photinea (*Photinia* sp.), holly (*Ilex* sp.), ferns of the family Polypodiaceae, schefflera (*Schefflera* sp.), aglaonema (*Aglaonema* sp.), cotoneaster (*Cotoneaster* sp.), barberry (*Berberis* sp.), waxmyrtle (*Myrica* sp.), abelia (*Abelia* sp.), acacia (*Acacia* sp.) and bromeliades of the family Bromeliaceae, and other commercial cultivars, hybrids and new developed cultivars.

CPAS has proven to be unexpectedly potent inhibitors of ethylene action on plants, fruits and vegetables, even when applied at low concentrations. Among other things, this compound is soluble and stable in water that enables to use a variety of methods for delivery an active substance to a plant, a cut fruit, and a cut vegetable, a cut flower. All objects can be brushed or dipped with CPAS aqueous solution or can be sprayed with that solution, addition of surfactant may improve penetration of the inhibitor. Additionally a cut surface of a fruit, a vegetable, and a flower can be dipped in CPAS solution for definite time.

Synthesis of water soluble 3-(1-cyclopropenyl) propanoic acid and its sodium or other positively charged (monovalent or bivalent) counter-ion salt is described below.

Analysis of the literature showed the simplest and the most reliable method of preparation of cyclopropene compounds is the elimination of three bromine atoms from 1,2,2-cyclopropane or its derivatives by the action of lithium organic compounds. The 1,2,2-tribromocyclopropane compounds are prepared by reaction of dibromocarbene with 2-bromo-1-alkene or its derivatives. Therefore, proceeding from commercially available reagents, the production of the ordered compound consists of three main synthesis steps: The first is preparation of 4-bromo-4-pentenoic acid or its derivative; the second step is production of 3-(1-cyclopropenyl) propanoic acid, and third step is conversion of this acid into sodium salt. Other salts, such as lithium, sodium, potassium, ammonium, calcium, magnesium, and positively charged counter-ions comprising e.g., at least one sulfate or phosphate molecules, salts are possible. Organic salts are also possible, comprising inter alia positively charged alkyl-containing compounds.

The total scheme of synthesis according to one embodiment of the invention comprises the following six stages, here provide, for example and in a non-limiting manner, for the synthesis of water soluble sodium CPAS:

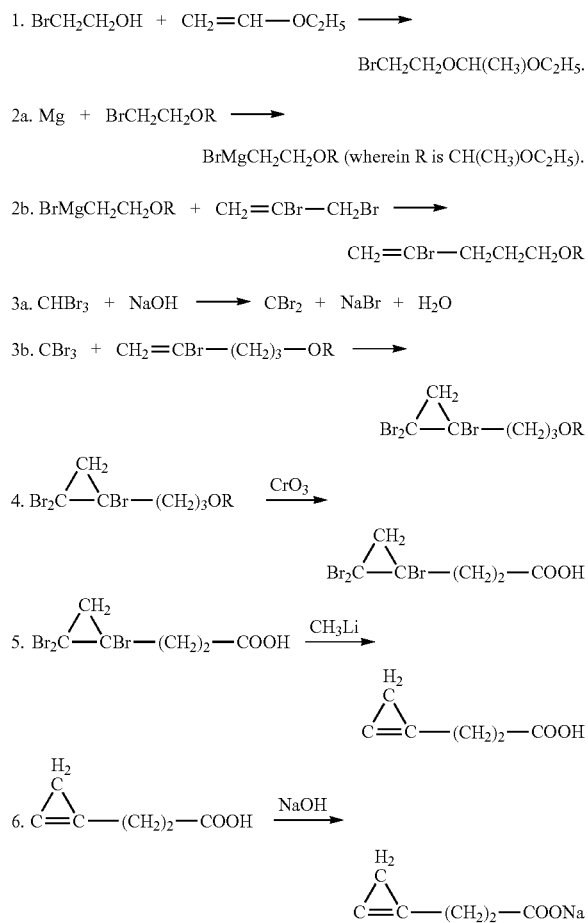

The structure of the obtained final product is demonstrated by several spectral methods: $^1$H, $^{13}$C, $^{23}$Na NMR, MS, IR-spectroscopy. Purity is established by HPLC and HPTLC methods. About 0.2 g of 3-(1-cyclopropenyl)propanoic acid has been obtained and the method of its purification is being developed.

The present invention is explained in greater detail in the following non-limiting examples.

Example 1

In order to determine the minimum effective concentration of water soluble CPAS in antagonizing ethylene action, the test was implemented using mature but not ripe fruits: green banana fruit; green avocado 'Hass' fruit; and mature but not ripe peach fruit. Cut flowers: carnation; carnation petals; and petunia flowers. Tomato seedlings; and citrus leaf explants. The above listed plant materials underwent treatments with CPAS solution±ethylene exposure. Minimum apparent concentrations of CPAS (µg mL$^{-1}$) and the time of provided protection (days) for those plant materials are presented in Table 1.

TABLE 1

Minimum apparent concentrations of CPAS (µg mL$^{-1}$) and the time of provided protection (days).

| Plant material | Parameters | Mode of application | Ethylene treatment | Concentration (µg mL$^{-1}$) | Protection time (days over control) |
|---|---|---|---|---|---|
| Banana fruit | Peel color | brushing | + | 200 | 6 |
| Avocado fruit | Peel color | Loading | + | 100 | 5 |
| Peach fruit | Firmness | Spraying | − | 10 | 4 |
| Carnation flower | Vase life | Loading | − | 0.8 | 10 |
| Carnation flower petal | Senescence | Loading | + | 81 | 11 |
| Petunia flower | Vase life | Loading | + | 98 | 17 |
| Tomato leaf | epinasty | spraying | + | 160 | *+++ |
| petiole | epinasty | Loading | + | 9 | *+++ |
| Citrus leaf | abscission | Loading | + | 32 | 7 |
| abscission | abscission | Dipping | + | 42 | 2 |

*Note:
+ = weak effect;
++ = medium effect;
+++ = strong effect

Figure 2:
FIG. 2 is a photograph of CPAS-treated and untreated carnation cut flowers.
Figure 2:
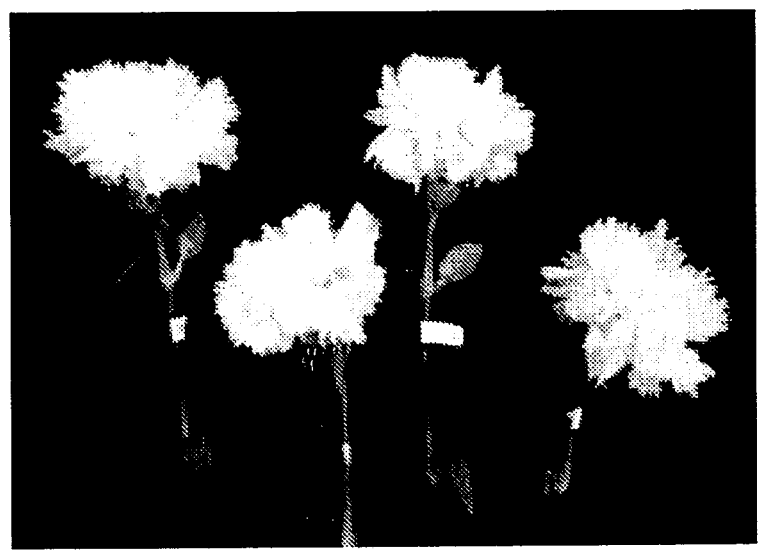
Figure 3:
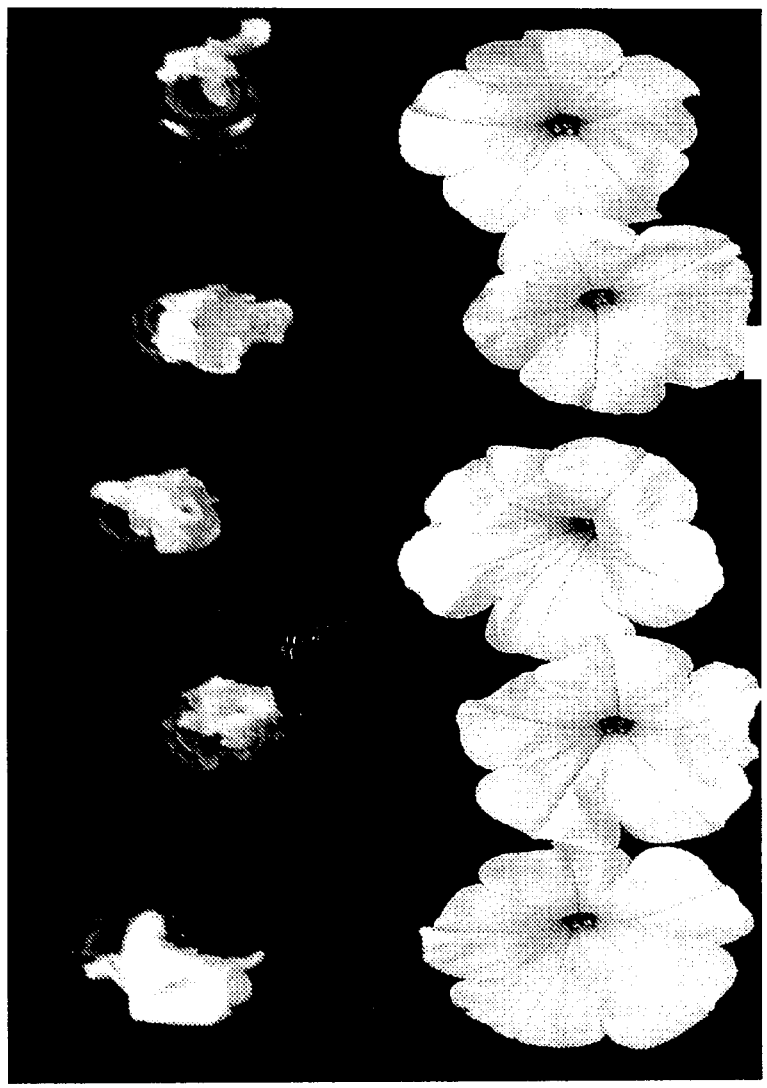
FIG. 3 is a photograph of CPAS-treated and untreated petunia cut flowers.
Figure 6:
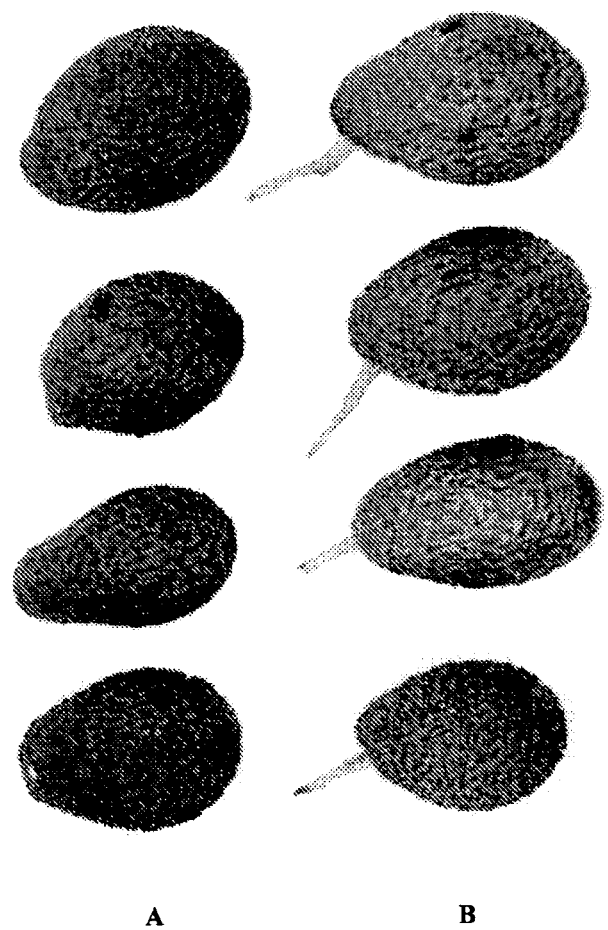
FIG. 6 is a photograph of CPAS-treated and untreated avocado fruits.

Each kind of the model plants was exposed to different concentrations of CPAS in an aqueous solution for 6-18 h as a pre-treatment following exposure for 24 h to different concentration of ethylene. In the case of banana and avocado fruits, the peel was brushed with different concentrations of CPAS aqueous solution, in the presence of commercially available Tween 20 surfactant (0.025%) as pre-ethylene treatment, and the delay in days elapsed until color breakdown (from green to yellow in banana—Table 1, FIG. 4; and from green to black in avocado—Table 1, FIG. 6) over air control was recorded as a criterion of the efficiency of the ethylene antagonist. In the case of peach fruit, the surfactant BAS 70 (generously supplied by BASF, Germany) was used. The results were recorded after incubation of 2-4 days in controlled conditions (Table 1, FIG. 11). When using cut flower models (FIGS. 1-3) CPAS aqueous solutions±surfactants was applied by loading either the cut flower or the isolated petals for 18 h in CPAS aqueous solutions prior to ethylene treatment. The number of days of the delay of senescence of the tested plant materials over water control was recorded, by following the visual wilting of the flowers. Tomato seedlings were sprayed with CPAS aqueous solutions in the presence of commercial available 'Kinetic' organo-silicone surfactant blend, kept for calibration in a growth chamber for 8-10 hr before spraying with CPAS solution or before loading CPSA by excised seedlings via their lower stem cut surface (Table 1, FIG. 10) in order to antagonize ethylene-induced epinasty of leaf petioles (Table 1, FIGS. 8-9). In the case of citrus leaf explants, abscission was tested at the laminar abscission zone. CPAS in aqueous solution, was either pre-treated by direct loading of the treatment solutions into the proximal side of the explant for 17 h, or by dipping the whole explant in the tested solutions for 30 to 60 sec in the presence of commercially available Tween 20 TM surfactant (0.025%. In all cases, a significant delaying action of ethylene-induced responses, was recorded in all the plant systems examined (Table 1, FIG. 7). In further examples, the concentrations of the CPAS aqueous solutions were used in the range of the results obtained in the above experiment.

Example 2

The following test was designed to further establish the ability of water soluble CPAS in aqueous solution to delay the ethylene-induced senescence of isolated carnation petals. The experiment was carried out in a growth chamber to ensure optimal environmental conditions (light, temperature and relative humidity). Carnation petals were loaded with CPAS by dipping their cut surface for 18 hr in aqueous solution containing 81 µg mL$^{-1}$ of CPAS. Untreated petals that were held in water. After 18 hr the treated petals transferred to water. Afterwards all petals were exposed for 24 hr to ethylene (5 µl L$^{-1}$). At the end of treatment the petal with their cut surface dipped in water were kept at 22° C. and 80% RH under continuous fluorescent light for assessment of their senescence value. Photos were taken on day 6 (untreated—FIG. 1A, treated FIG. 1B).

The ethylene antagonistic effect of CPAS in aqueous solution measured after 6 days was highly significant. No toxic symptoms were observed in the course of the experiment.

Example 3

Carnation cut flowers treated by dipping cut surface for 18 hr in aqueous solution containing 8 µg mL$^{-1}$ of CPAS. Untreated flowers were held in water. After treatment all flowers are kept in water at 22° C. and 80% RH under continuous fluorescent light for assessment of their vase life. Photo was taken on day 14. Obtained results show longevity increase of carnation cut flowers during vase life in the presence of CPAS in aqueous solution (FIG. 2B) in comparison with untreated flowers (FIG. 2A).

Example 4

Short stem petunia cut flowers were loaded with water soluble CPAS by dipping cut surface for 18 hr in aqueous solution containing 98 µg mL$^{-1}$ of CPAS. Untreated flowers were held in water. After 18 hr loading the treated flowers were transferred to water. Then the flowers were exposed for 24 hr to ethylene (5 µg L$^{-1}$) to hasten flower senescence. At the end of treatment flowers with their cut surfaces dipped in water were incubated at 22° C. and 80% RH under continuous fluorescent light for assessment of their vase life. Photo was taken on day 14 (untreated—FIG. 3A, treated FIG. 3B).

Petunia is known for its sensitivity to ethylene and thus is often used as a model system for studying ethylene responses. The results of this experiment are in full agreement with the previous experiments, adding more support of the efficiency of CPAS as ethylene antagonist when applies in soluble form in water.

Example 5

Banana fruits were treated by brushing with aqueous solution of water soluble CPAS (200 µg mL$^{-1}$). After 18 hr all treated and untreated fruits were exposed to ethylene (300 µL$^{-1}$) to hasten ripening. All fruits were ventilated and held in air at 22° C. and 92% RH for assessment of their ripening value. Photos were taken on day 12 (untreated—FIG. 4A, treated FIG. 4B).

Figure 5:
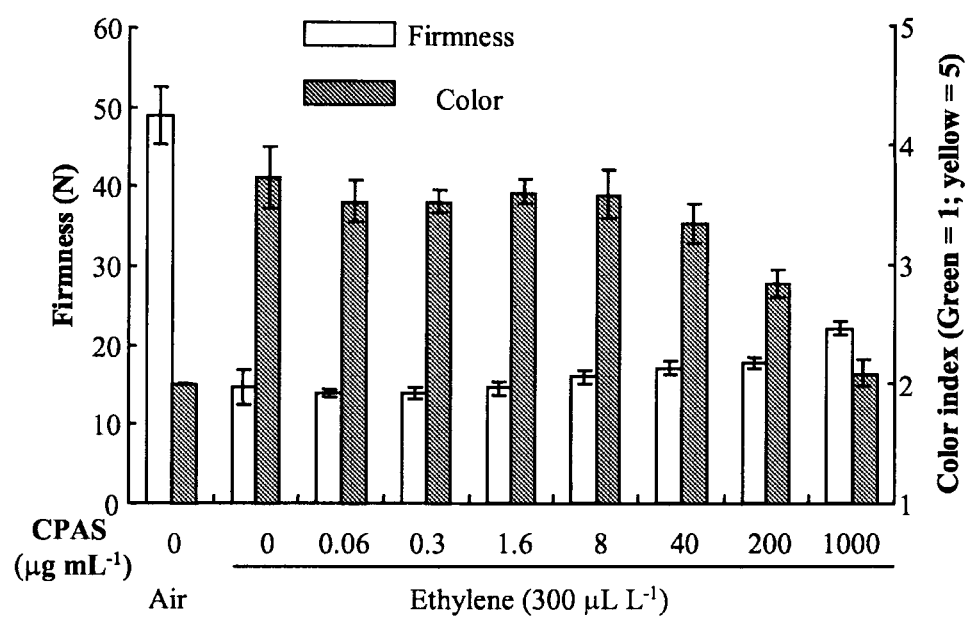
FIG. 5 is a diagram showing dependence of firmness and color of banana fruits on CPAS and ethylene loading.

Additionally, banana fruits were treated by brushing with aqueous solution of CPAS (0.6 to 1000 µg µL$^{-1}$, and commercially available surfactant Tween 20 [0.025%]) and after 18 hr were exposed to ethylene (300 µL/L$^{-1}$) for 24 hr to hasten ripening. Fruits were kept at 24° C. and 92% RH. The fruits kept in air and treated by CPAS only served as comparative ones. Results were collected on day 7 (FIG. 5A).

Figure 4:
FIG. 4 is a photograph of CPAS-treated and untreated banana fruits.

Aqueous solution of CPAS (1000 µg mL$^{-1}$) was ineffective in delaying the decrease in fruit firmness, meaning that it did not extend the shelf life of the fruit. Nevertheless, it was found that it significantly delayed the color break of the fruit (FIG. 4). FIG. 5A represents a diagram showing dependence of firmness and color of banana fruits in relation to CPAS and ethylene exposure. As seen there are the dual negative and positive effects of CPAS in aqueous solution on the firmness and color, respectively. Firmness dropped significantly below 25 N and the fruits were completely edible after 18 h air pre-treatment following by 24 h exposure to ethylene. The pattern of color break was just the opposite and was almost completed at that point. Addition of CPAS did almost not prevent, in all of its concentration, the decrease of fruit firmness, while it was effective at the higher concentrations in preventing the color break.

Example 6

"Hass" avocado fruits with long peduncles were loaded with water soluble CPAS by dipping the peduncle cut surface for 30 hr in aqueous solution containing 100 µg/mL$^{-1}$ of CPAS. The untreated fruits with peduncles immersed in water. After the treatment with CPAS all fruits were exposed for 24 hr to the ethylene (250 µL L$^{-1}$). Afterwards the fruits were held at 24° C. and 92% RH for assessment their maturity parameters (peel color change and pulp firmness) and abscission of the peduncle. Photos were taken on day 5 after treatment (untreated—FIG. 6A, treated FIG. 6B).

Towards ripening avocado green skin color turns to purple-black. Fruits with long peduncles were immersed in CPAS in aqueous solution as pre-treatment followed by ethylene treatment. Although the skin color development and peduncle abscission were significantly delayed by the antagonist, a little delaying effect on fruit softening was recorded, probably due to limited penetration of the compound into the bulky tissue.

Thus, obtained experimental results confirm that CPAS is an effective ethylene antagonist. Application of an effective ethylene response-inhibiting amount of CPAS enables to extend harvest season of crops, prolong storability and shelf life of fruit and the vase life of cut flowers, and also probable herbs and leafy vegetables. However, CPAS is the only compound that can be used practically due to its solubility in water, stability, and high potency to inhibit ethylene responses in various plant systems under various conditions.

Example 7

The application of water soluble CPAS to citrus leaf explants was studied under air, antagonizing endogenous ethylene-induced abscission, comparing two methods of applications; either by dipping their petiole cut surfaces for 6 h in CPAS aqueous solution, or by dipping the whole explants for 30 sec. in the same treatment solution plus or minus a surfactant. In this experiment Tween-20 (0.025%) was chosen as surfactant, but any un-ionic surfactant may be chosen. The experiment indicates, as expected, that surfactants improve the penetration into plant tissues. However, if application is preferred via a cut surface like with cut flowers, there is no need to add a surfactant to the treatment solution (FIG. 7).

Figure 7:
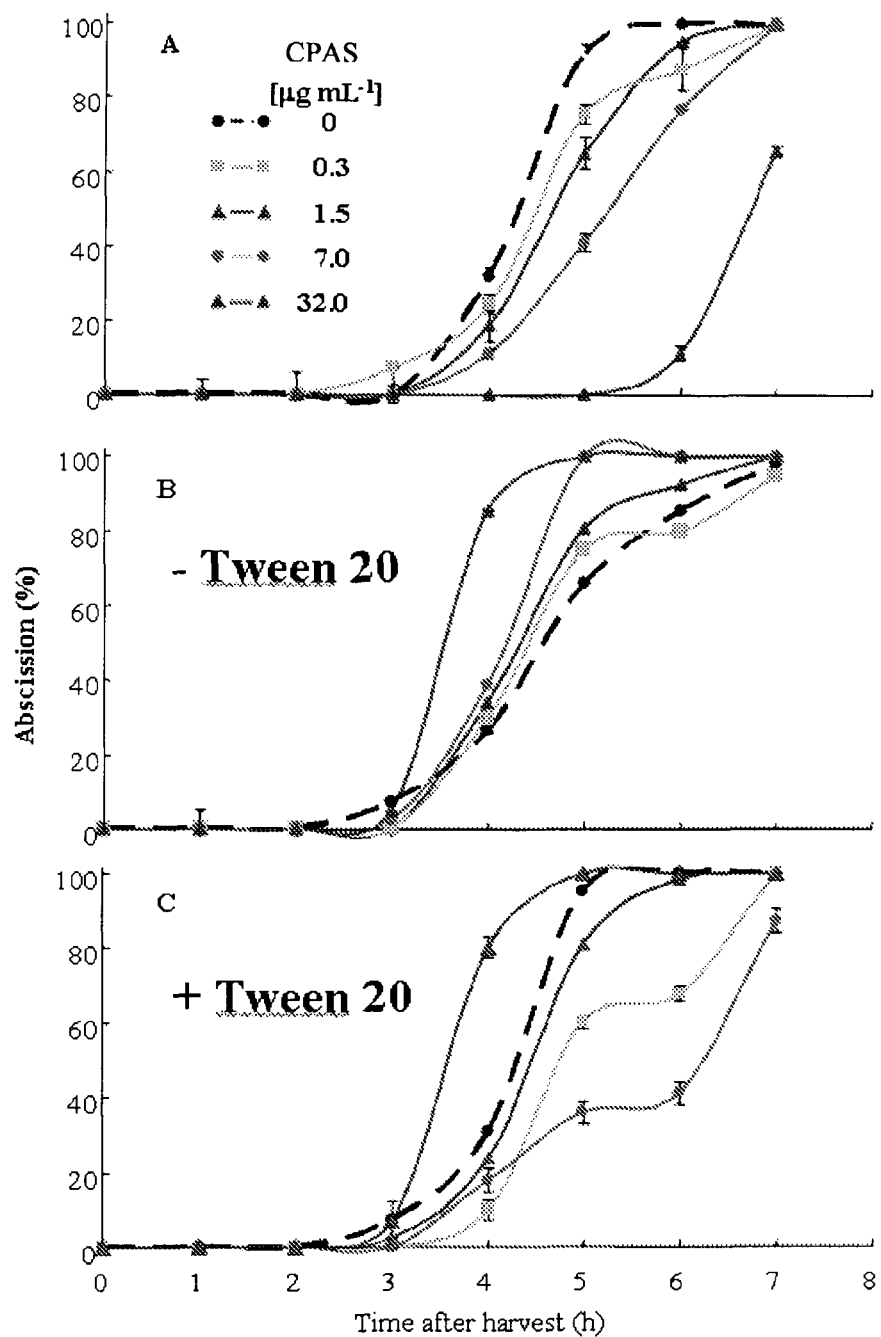
FIG. 7 is a figure showing the effects of CPAS on delaying citrus leaf explants abscission.
Figure 8:
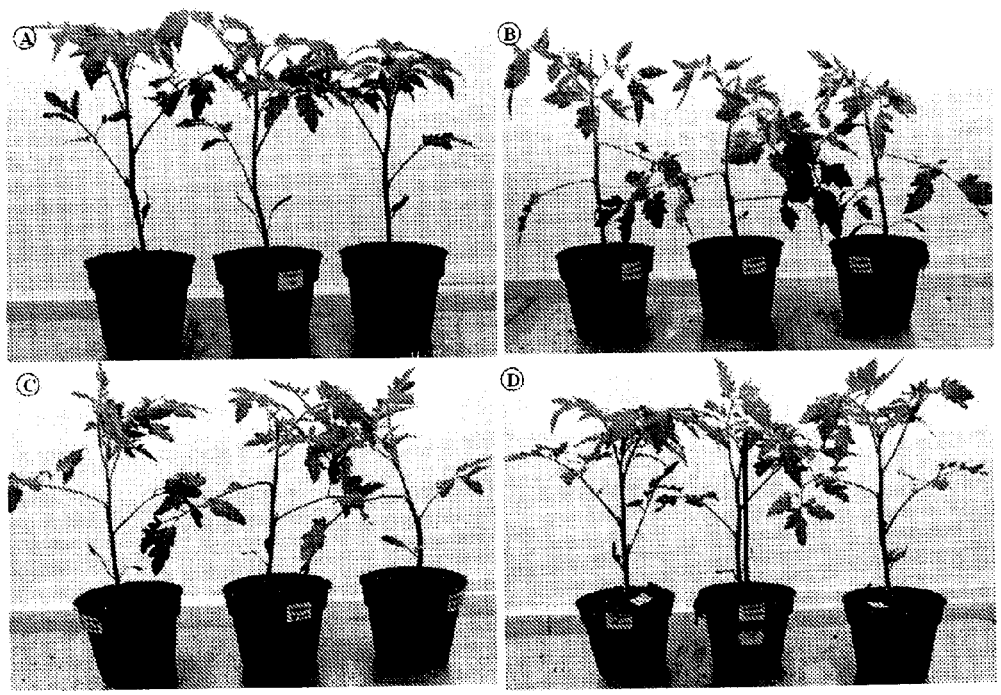
FIG. 8 presents the effect of spraying tomato plants with CPAS on ethylene-induced leaf petioles epinasty.

FIG. 7 represents a set of three figures, wherein explants are loaded with CPAS by dipping their petiole cut surfaces for 6 h in CPAS aqueous solution (A); dipped for 30 sec. in the same treatment solution (B); and treated as in B, but including Tween-20 [0.025%] (C).

Example 8

Another plant model that was selected for testing the efficiency of water soluble CPAS was 3 weeks old tomato seedlings. These seedlings are very sensitive to ethylene that induces an epinastic effect of the young leaves (see FIG. 8). If CPAS should be active it should antagonize this effect. The experiments were so designed that they should also answer whether the soluble ethylene antagonist could be supplied by spraying. For this reason surfactants were added to the spraying solution, as is routinely done in the field when chemicals like plant growth regulators are used. In the abscission study (example 7) we showed that when explants were dipped in the treatment solution the CPSA effect was more pronounced (FIG. 7). The design of the experiment included loading treatments for comparison (FIG. 9).

For the spraying experiment (FIG. 8) tomato plants from green house (3 weeks old) were brought for calibration in a growth chamber (8-10 hr, at 22° C. and 80% RH, under continuous fluorescent light). Thereafter, the whole plants were sprayed with 0 (A and B), 80 (C), 160 (D) µg mL$^{-1}$ of CPAS dissolved in phosphate buffer (pH 7.8; 10 mM) containing 0.1% "Kinetic" as surfactant. The use of the buffer helps to stabilize the pH but is not obligatory. The use of tap water is also possible. After 18 hr, the pre-treated plants (B, C and D) were exposed to 1 µl L$^{-1}$ ethylene for 24 hr. Plants sprayed with the same treatment solution without CPAS±ethylene (A and B), served as air or ethylene controls.

Figure 9:
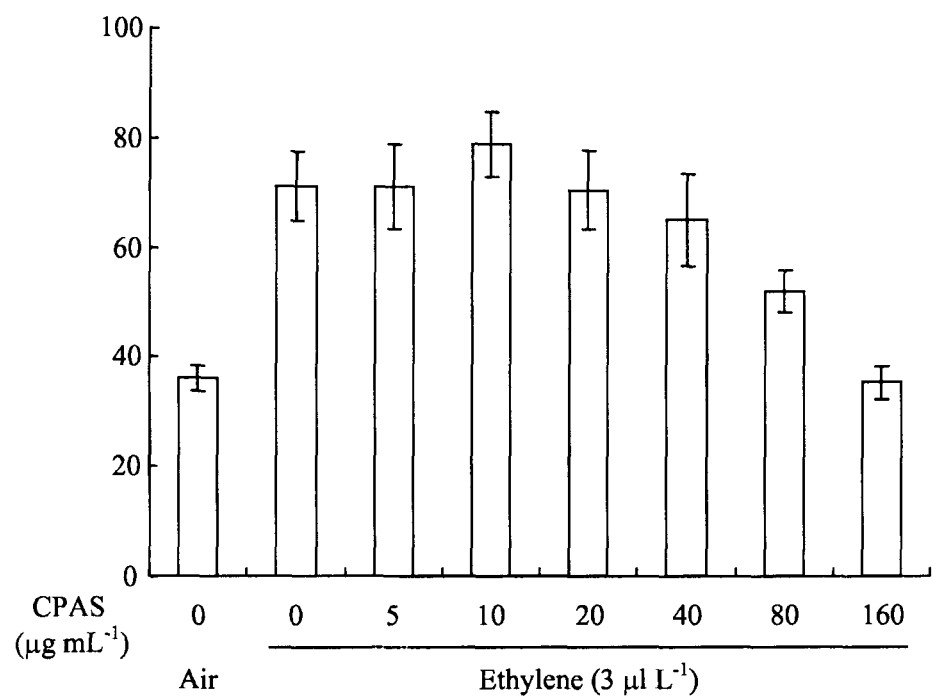
FIG. 9 presents the effect of spraying tomato plants with CPAS on ethylene-induced leaf petiole epinasty.

In a second experiment the changes of the degree of the petiole from the branch, that expresses the epinastic response, was calculated (FIG. 9). The experimental conditions are as described for FIG. 8, except that after the pretreatment with CPAS, the tomato plants were exposed to 3 µl L$^{-1}$ ethylene for 24 hr, and at the end of the treatments the plants were transferred to a shelf for assessment of each leaf petiole apinasty (the angle between the branch and leaf petiole). Values are mean±standard error (n=9-12).

Figure 10:
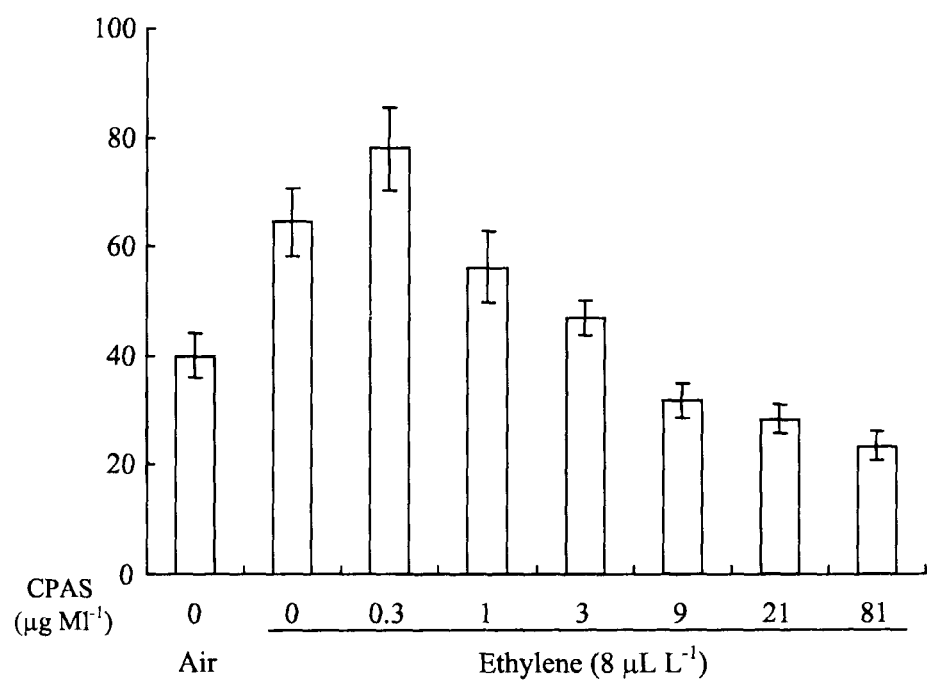
FIG. 10 presents the effect of loading of an excised tomato plants with CPAS on ethylene-induced epinasty of leaf petiole; and, FIG. 11 presents the effect of spraying CPAS on peach fruits.

Tomato plants from green house (4 weeks old) were brought in order to study the effects of CPAS loading to excised tomato plant (about 15 cm. long stem) on ethylene-induced epinasty of leaf petioles. Reference is now made to FIG. 10 presenting the effect of loading of an excised tomato plants with CPAS on ethylene-induced epinasty of leaf petiole. All other details are as described in example 8, except that at the end of the treatments the cut plants with their cut surface in tape water were transferred to a shelf for assessment of each leaf petiole apinasty (angle between the branch and leaf petiole), values are mean±standard error (n=9 to 12). Each plant was cut, after pre-calibration (as defined above) at its base and immediately renewed its cut surface under tape water and placed into 30 ml tape water for 8-10 hr calibration in light and humid condition. Thereafter, the branches were dipped with their cut surface into 15 ml phosphate buffer (pH 7.8; 10 mM) containing 0 to 81 µg mL$^{-1}$ of CPAS. After 18 hr loading, all the pre-treatment branches were transferred to tape water and exposed to ethylene (3 µl L$^{-1}$) for 24. Explants that were loaded with the same treatment solution without CPAS served as air or ethylene controls.

These three experiments demonstrate that CPAS can be used as a water soluble spraying agro-technical tool and that in the presence of surfactant it easily penetrates the tissue via the cuticle of vegetative plant organs.

Example 9

Figure 11:
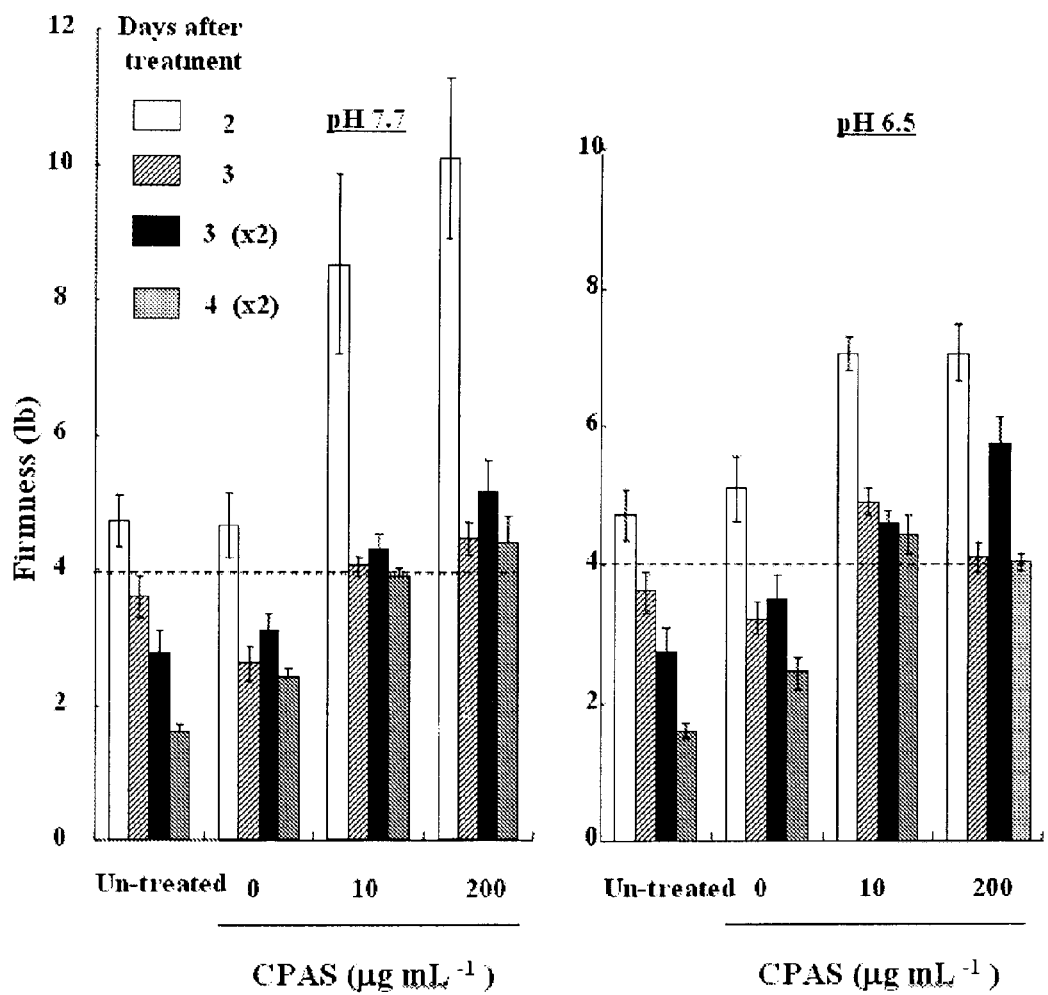
Figure 12:
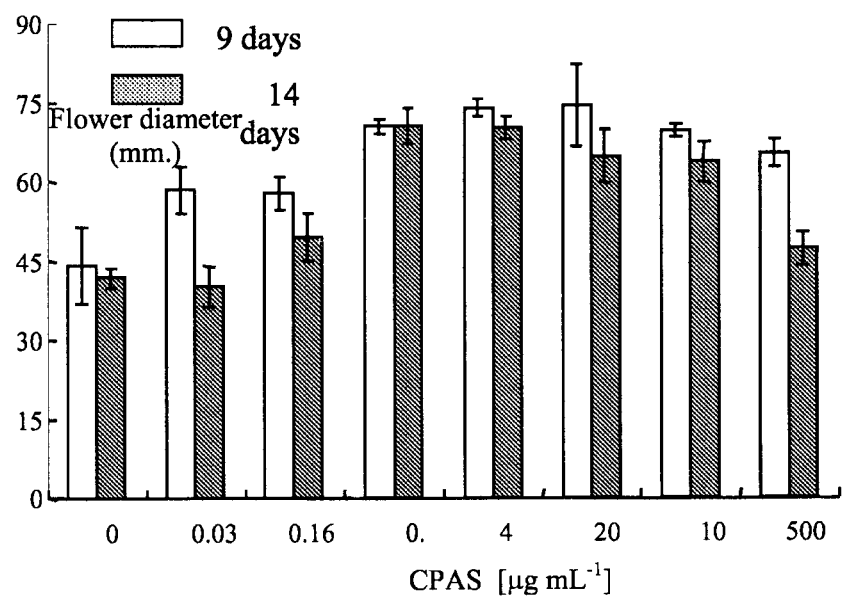
FIG. 12 presents the effect of loading CPAS on the inflorescence diameter of carnation cut flowers.
Figure 13:
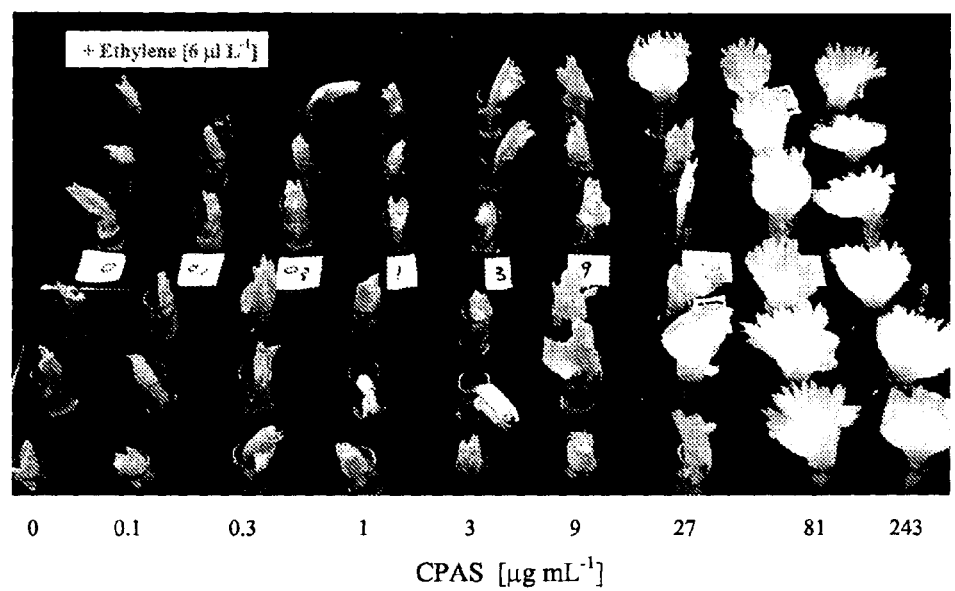
FIG. 13 presents the effect of loading CPAS on delaying ethylene-induced senescence of excised petals, 14 days after treatment.
Figure 14:
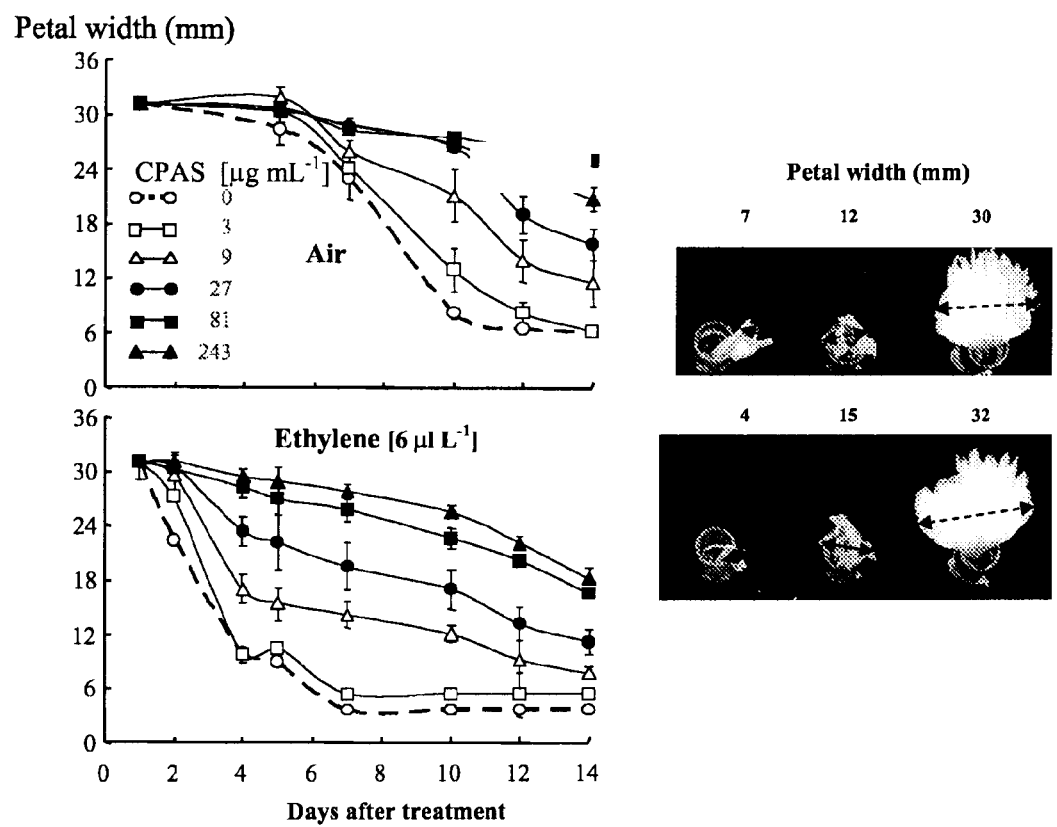
FIG. 14 presents the effect of loading CPAS followed by air or ethylene treatment on excised petals
Figure 15:
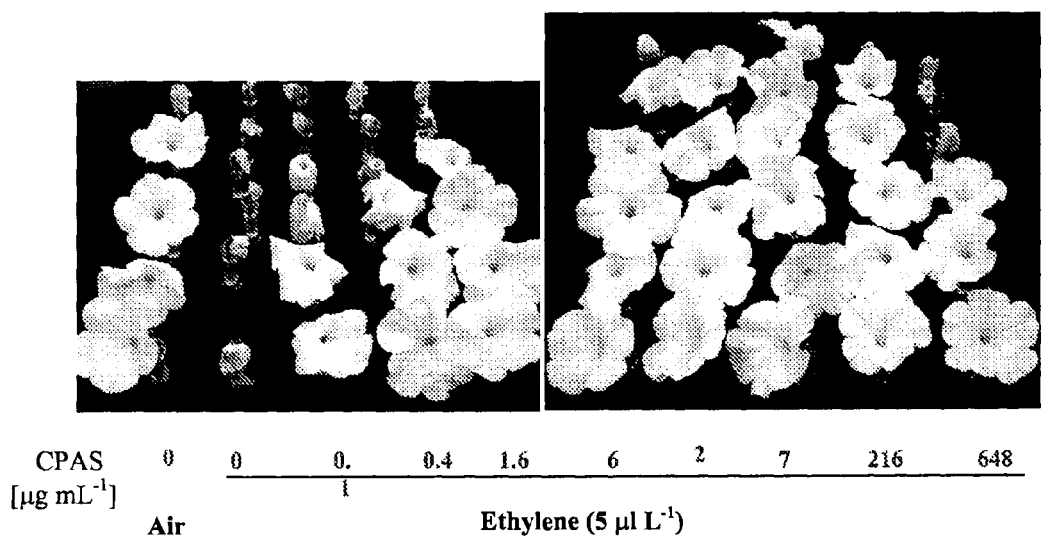
FIG. 15 presents the effect of loading of CPAS on delaying ethylene-induced senescence of Petunia flowers, 15 days after treatment
Figure 16:
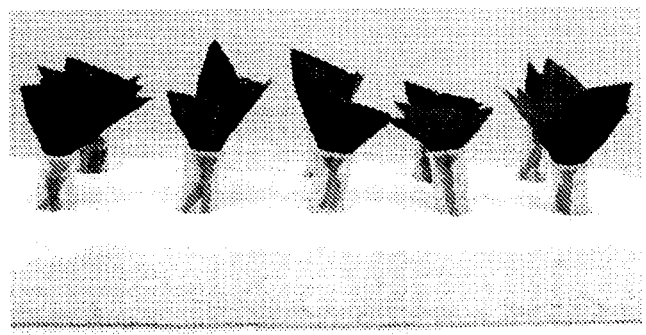
FIG. 16 presents model systems with citrus leaf explants; (A) Loading: Leaf explants were loaded with the inhibitor for 6 h in tap water containing various concentrations of CPAS by immersing the petiole cut surface into the treatment solution; (B) Dipping: Leaf explants were immersed for 30 sec in tap water containing various concentrations of CPAS plus Tween-20 (0.025%)
Figure 16:
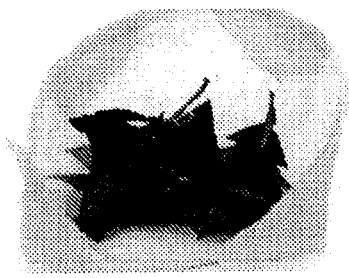
Figure 17:
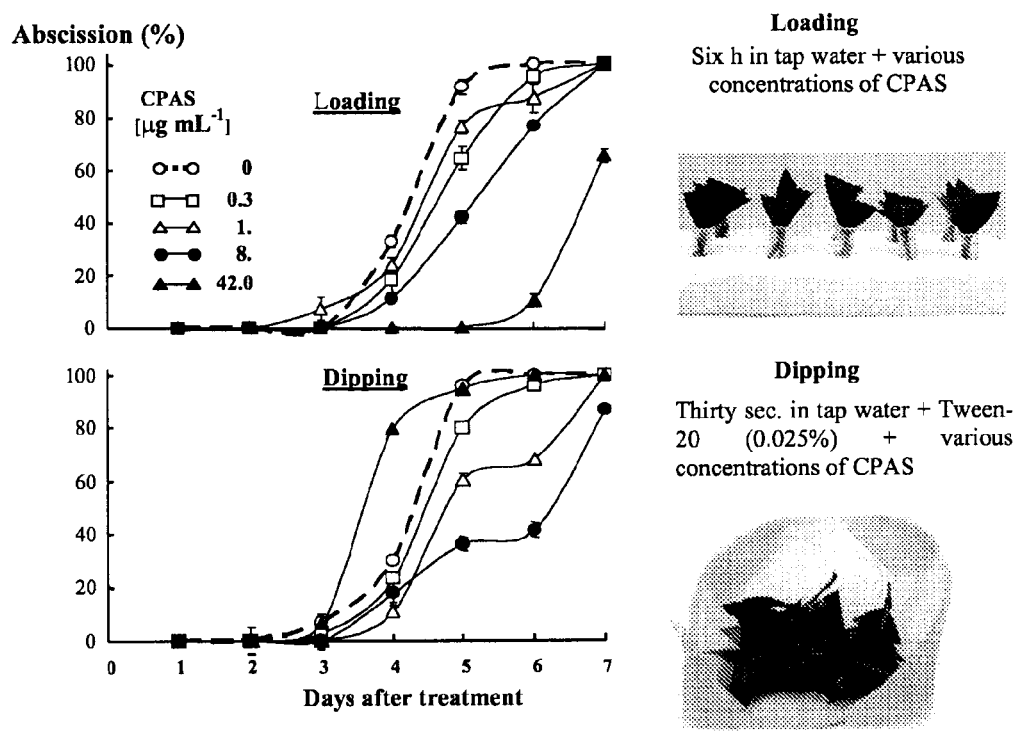
FIG. 17 presents the effect of CPAS on delaying abscission of citrus leaf explants.
Figure 18:
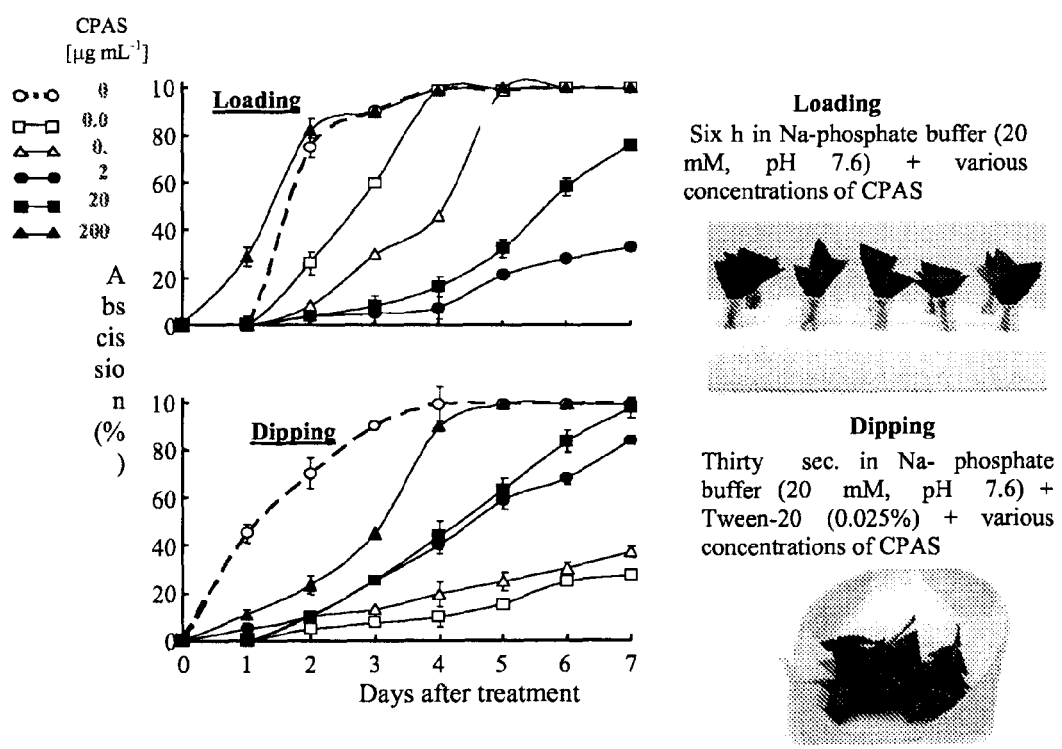
FIG. 18 presents the effect of buffer solution of CPAS on delaying abscission of citrus leaf explants.
Figure 19:
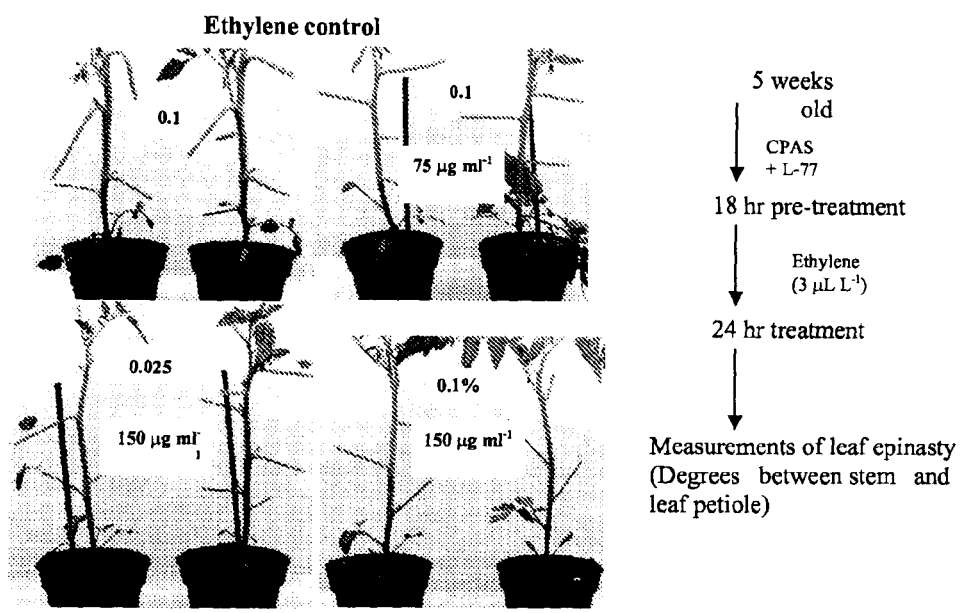
FIG. 19 presents the effect of spraying tomato plants with CPAS on ethylene-induced leaf petioles epinasty; Five weeks old plants from green house were pre-treated by spraying with K-phosphate buffer (pH 7.8; 10 mM) containing 0.025 to 0.1% L-77 surfactant+CPAS; after 18 hr, the pre-treated plants were exposed to ethylene 3 µL L-1 for 24 hr.
Figure 20:
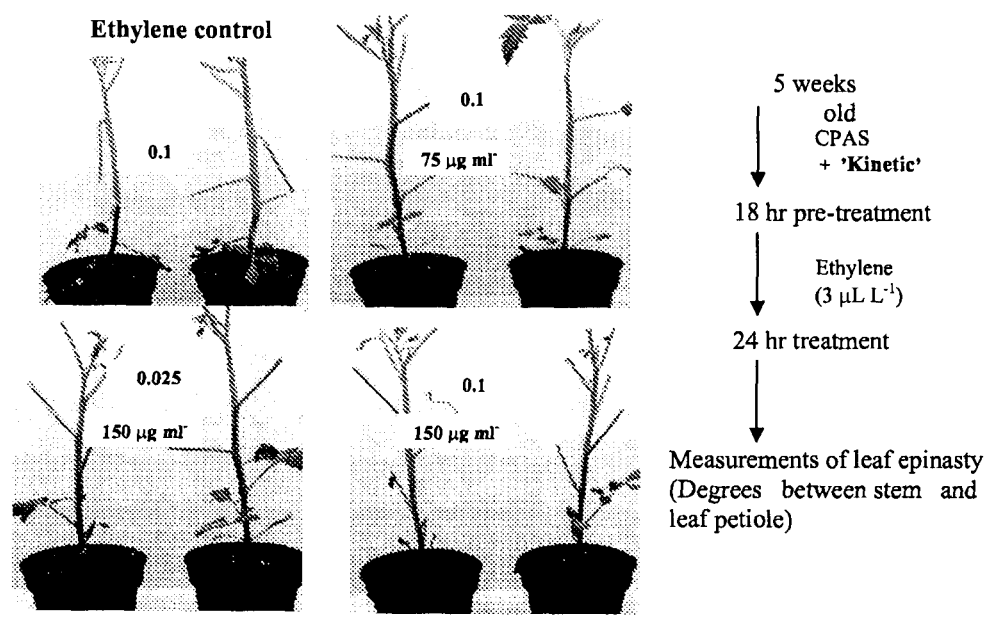
FIG. 20 presents the effect of spraying tomato plants with CPAS on ethylene-induced leaf petioles epinasty; Five weeks old plants from green house were pre-treated by sprayed with K-phosphate buffer (pH 7.8; 10 mM) containing 0.025 to 0.1% 'Kinetic' surfactant+CPAS; after 18 hr, the pre-treated plants were exposed to ethylene 3 µl L-1 for 24 hr.
Figure 21:
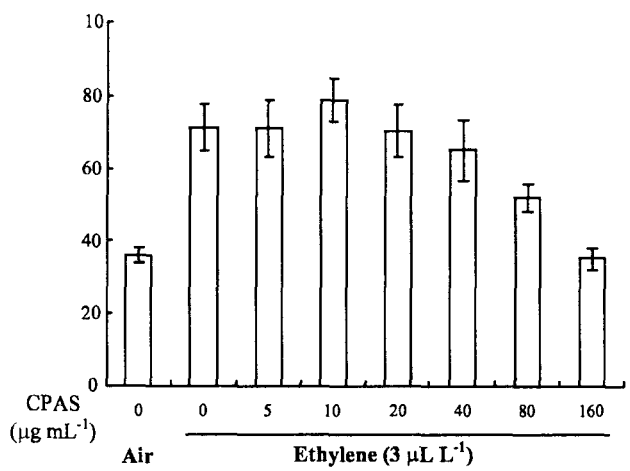
FIG. 21 presents the effect of spraying tomato plants with CPAS on ethylene-induced leaf petiole epinasty.
Figure 21:
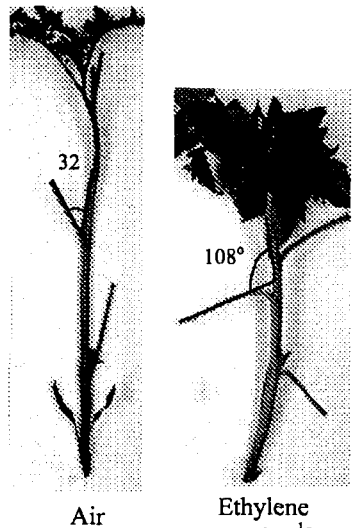
Figure 21:
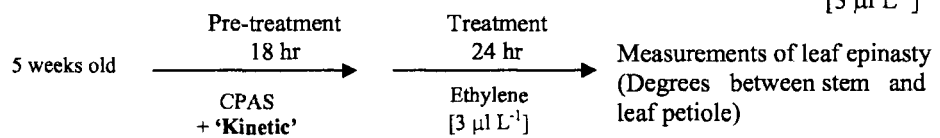
Figure 22:
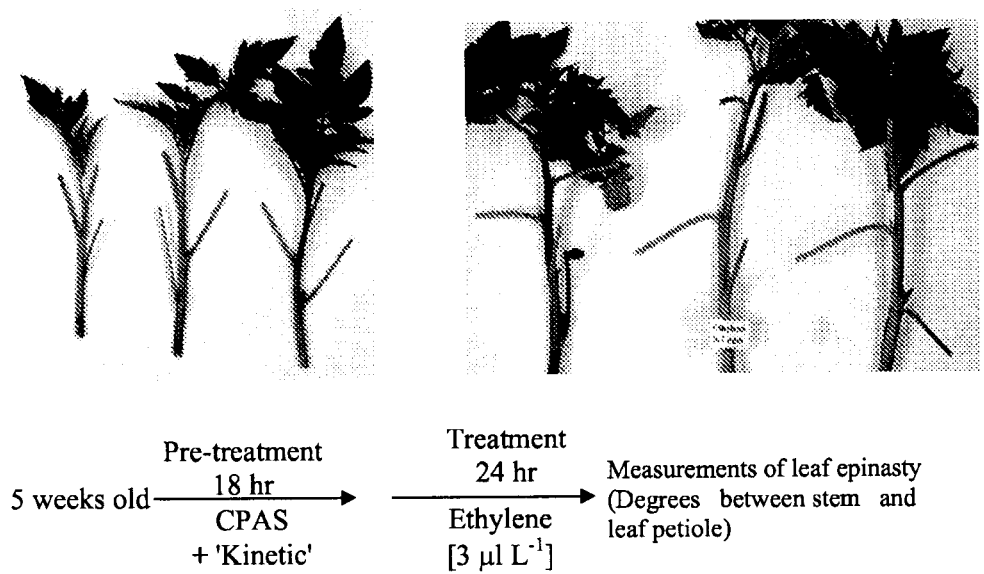
FIG. 22 presents the effect of loading tomato branches with CPAS on ethylene-induced leaf petiole epinasty.
Figure 23:
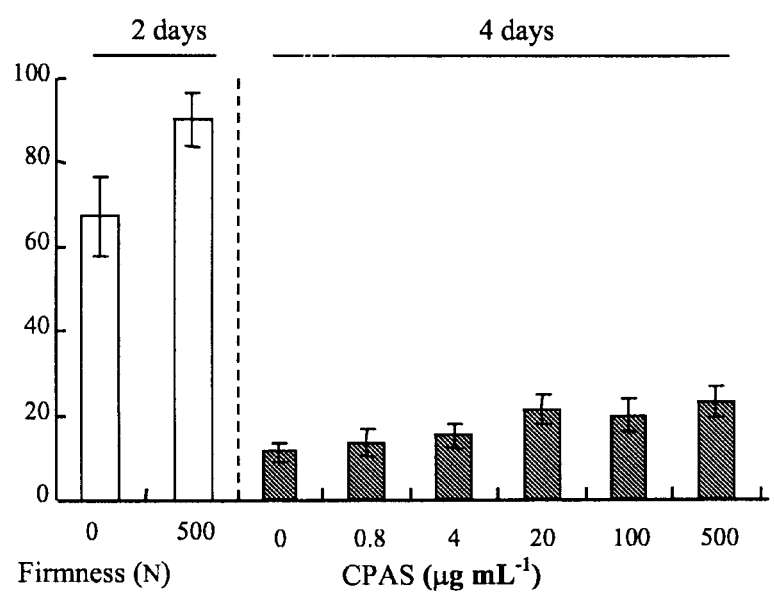
FIG. 23 presents the effect of brushing with CPAS on delaying ethylene-induced ripening of avocado 'Hass' cv., 5 days after treatment; Green mature 'Hass' cv. fruits were pre-treated (B) by brushing gently their peel with tap water CPAS solution (100 µg mL-1+0.1% 'Kinetic' as a surfactant). After 18 hr, Untreated (A) and the pre-treated fruits (B) were exposed to ethylene (250 µL L-1) for 24 hr.
Figure 24:
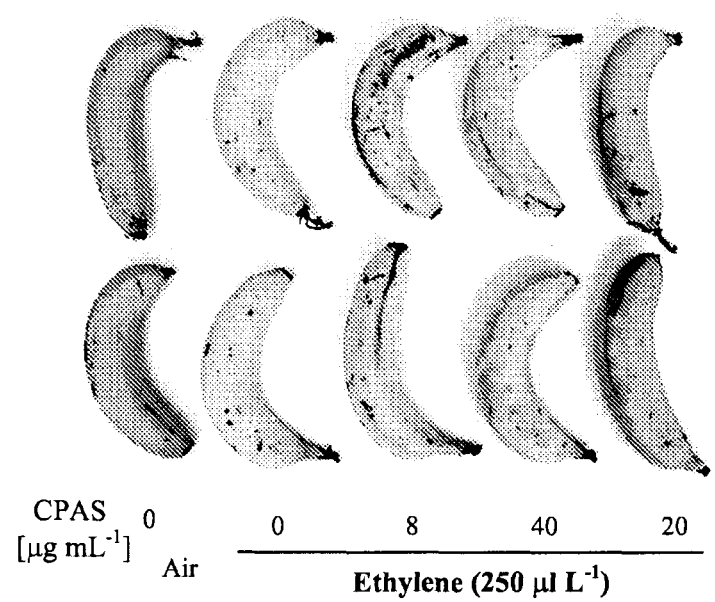
FIG. 24 presents the effect of brushing with CPAS on delaying ethylene-induced ripening of banana, 10 days after treatment; Green banana fruits were pre-treated by brushing gently their peel with tap water CPAS solution (+0.025% Tween 20 as a surfactant). After 18 hr, the pre-treated fruits were exposed to ethylene (250 µL L-1) for 24 hr.
Figure 25:
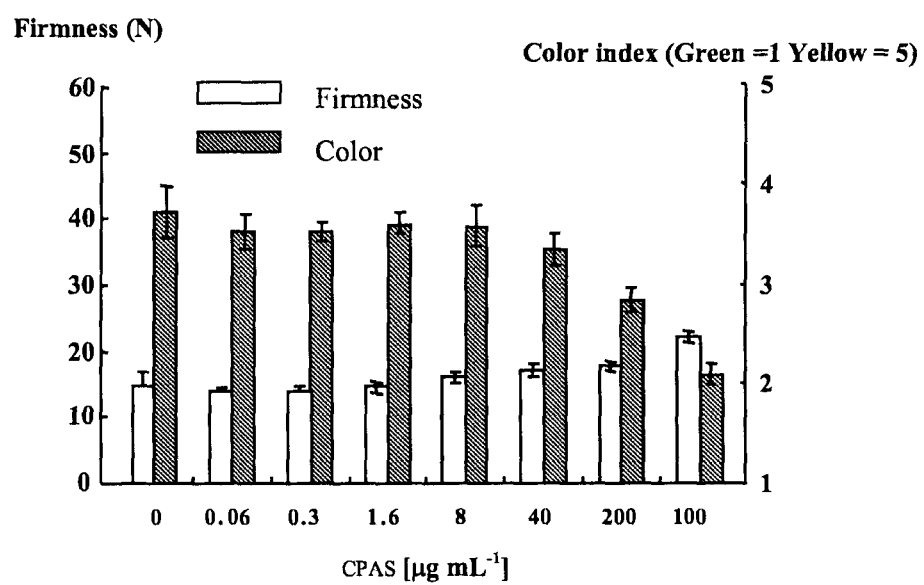
FIG. 25 presents the effect of CPAS on delaying ethylene-induced ripening of banana, 10 days after treatment; Green banana fruits were pre-treated by brushing gently their peel with tap water CPAS solution (+0.025% Tween 20 as a surfactant). After 18 hr, the pre-treated fruits were exposed to ethylene (250 µL L-1) for 24 hr.

The use of surfactants was also tested by spaying mature, but not ripe peach fruits (FIG. 11). This experiment was also designed to study the ability of water soluble CPSA to antagonize the climacteric rise of endogenous ethylene, and thus to extend the shelf life (delay of softening) of the fruit. Peach was selected as an additional ethylene sensitive climacteric fruit. In this experiment the efficiency of the penetration of aqueous solution of CPAS was further studied.

Peach fruits were harvested and brought to the lab and immediately sprayed with different concentrations of CPAS solution (K-phosphate buffer, 20 mM, and 0.1% organo-silicone surfactant, namely BAS 90370S by BASF Germany), and kept at 22° C. and 90% humidity for up to 4 days. Untreated fruits were served as control. The following treatments were: (a) spraying at 0 time and firmness checked after two days; (b) same as (a) but checking firmness after three days; (c) same as (a) with a second spray at the second day and checking firmness after 3 days; and (d), same as (c) with a second spray after one day and checking firmness after 4 days. Firmness was recorded by a penetrometer (chatillon, using a disc of 8 mm diameter), after removing a 15 mm square peel strip in order to allow measuring the firmness directly on the flesh of the fruit.

This example clearly demonstrated the ability of CPAS to penetrate into the fruit tissue, via its peel and expand the shelf life of climacteric fruits.

Thus, obtained experimental results confirm that CPAS is an effective ethylene antagonist. Application of an effective ethylene response-inhibiting amount of CPAS enables to extend harvest season of crops, prolong storability and shelf life of fruit and the vase life of cut flowers, ethylene morphological effects like leaf petiole epynasty, and also probable herbs and leafy vegetables. It is possible to conclude, based on the examples described above that CPAS is a compound that can be used practically either as a spraying agro-technical tool or for loading or dipping treatment in aqueous solution due to its solubility in water, stability, and high potency to inhibit ethylene responses in various plant systems under various conditions.

FIGS. 12 to 25 discloses that CPAS is very effective as ethylene antagonist when applied, inter alia, both by dipping and loading as also shown when the inhibitor is applied by spraying. Loading does not requires the addition of surfactant into the aqueous solution of the CPAS. The spraying of peach fruits with aqueous solution of CPAS-containing surfactant, has demonstrated that the application of the inhibitor is capable in delaying climacteric effect of ethylene on fruit repining, and consequently extends fruit shelf-life.

Effective measure of CPAS was found to be, in a non-limiting manner, from about 0.03 to about 1000 µg µL$^{-1}$. The CPAS was dissolve in an aqueous solution to an effective measure ranging from e.g., 0.1 to 200 (µg mL$^{-1}$).

Penetration (A) and Purity (B) of CPAS (A) The penetration of CPAS aqueous solution with and without surfactants into various plants was demonstrated as follows: a. banana fruit (Example 5); b. abscission of citrus leaf explants (Example 7); epinasty of tomato petioles seedlings (Example 8); and c. peach firmness (Example 9).

It was further found that the use of different nonionic surfactants significantly improved the penetration of CPAS into the tissue and improved is antagonizing ethylene-induced effects.

An effective measure of the surfactant was found to be in a non-limiting manner between about 0.025% (w/w) to about 0.1% (w/w)

(B) Purity—the aforesaid CPAS synthetic pathway was provided in two different batches, with about 90% purification, see Certificate Analyses as presented in FIG. 26A and FIG. 26B.

The invention claimed is:

1. A method of inhibiting an ethylene response in a plant, the method comprising applying to at least one portion of said plant an effective ethylene response-inhibiting amount of a water-soluble sodium salt of 3-(1-cyclopropenyl) propanoic acid, wherein said sodium salt of 3-(1-cyclopropenyl)propanoic acid is provided in an aqueous solution at a concentration of 0.1-200 μg/ml, and wherein said applying comprising preparing said aqueous solution of said sodium salt of 3-(1-cyclopropenyl)propanoic acid and applying said aqueous solution to the plant.

2. The method according to claim 1, wherein said applying is carried out by dipping at least a part of said plant in said solution.

3. The method according to claim 1, wherein said applying is carried out by spraying at least part of said plant with said solution.

4. The method according to claim 1, wherein said applying is carried out by irrigating or drop emitting at least a part of said plant with said solution.

5. The method according to claim 1, wherein said applying is carried out by brushing at least a part of said plant with said solution.

6. The method according to claim 1, wherein said ethylene response is fruit ripening.

7. The method according to claim 1, wherein said ethylene response is vegetable ripening.

8. The method according to claim 1, wherein said ethylene response is flower senescence.

9. The method according to claim 1, wherein said ethylene response is abscission.

10. The method according to claim 1, wherein said plant is a harvested fruit.

11. The method according to claim 1, wherein said plant is a harvested vegetable.

12. The method according to claim 1, additionally comprising admixing the sodium salt of 3-(1-cyclopropenyl) propanoic acid with a surfactant such that a surface-active aqueous solution containing said sodium salt of 3-(1-cyclopropenyl) propanoic acid is obtained.

13. The method according to claim 1, wherein said water soluble sodium salt of 3-(1-cyclopropenyl) propanoic acid is provided in the form of a powder.

14. A method of prolonging the life of a harvested fruit, the method comprising applying to the harvested fruit an effective life-prolonging amount of a water-soluble sodium salt of 3-(1-cyclopropenyl)propanoic acid, wherein said sodium salt of 3-(1-cyclopropenyl)propanoic acid is provided in an aqueous solution at a concentration of 0.1-200 μg/ml, and wherein said applying comprising preparing said aqueous solution of said sodium salt of 3-(1-cyclopropenyl)propanoic acid and applying said aqueous solution to the plant.

15. The method according to claim 14, wherein said applying is carried out by dipping at least a part of said harvested fruit in said solution.

16. The method according to claim 14, wherein said applying is carried out by spraying at least part of said harvested fruit with said solution.

17. The method according to claim 14, wherein said applying is carried out by brushing at least a part of said harvested fruit with said solution.

18. The method according to claim 14, wherein said applying is carried out by irrigating or drop emitting at least a part of said harvested fruit with said solution.

19. The method according to claim 14, wherein said water soluble sodium salt of 3-(1-cyclopropenyl) propanoic acid is provided in the form of a powder.

20. A method of prolonging the life of a cut flower, the method comprising applying to the cut flower an effective life-prolonging amount of a water-soluble sodium salt of 3-(1-cyclopropenyl)propanoic acid, wherein said sodium salt of 3-(1-cyclopropenyl)propanoic acid is provided in an aqueous solution at a concentration of 0.1-200 μg/ml, and wherein said applying comprising preparing said aqueous solution of said sodium salt of 3-(1-cyclopropenyl)propanoic acid and applying said aqueous solution to the plant.

21. The method according to claim 20, wherein said applying is carried out by dipping at least a part of said cut flower into said solution.

22. The method according to claim 20, wherein said applying is carried out by spraying at least part of said cut flower with said solution.

23. The method according to claim 20, wherein said applying is carried out by irrigating or drop emitting at least a part of said cut flower with said solution.

24. The method according to claim 20, wherein said applying is carried out by brushing at least a part of said cut flower with said solution.

25. The method according to claim 20, wherein said water soluble sodium salt of 3-(1-cyclopropenyl) propanoic acid is provided in the form of a powder.

26. A water soluble sodium salt of 3-(1-cyclopropenyl) propanoic acid.

27. The water soluble sodium salt of 3-(1-cyclopropenyl) propanoic acid according to claim 26, provided in the form of a powder.

28. A composition comprising the water soluble sodium salt of 3-(1-cyclopropenyl) propanoic acid according to claim 26, and a surfactant, wherein said water soluble salt is provided as a surface-active water soluble sodium salt of 3-(1-cyclopropenyl) propanoic acid.

29. A method of producing the water soluble sodium salt of 3-(1-cyclopropyl)propanoic acid according to claim 26, the method comprising (i) preparing 4-bromo-4-pentenoic acid or derivatives thereof; (ii) reacting said 4-bromo-4-pentenoic acid or derivatives thereof with dibromocarbene to produce a 1,2,2-tribromocyclopropane compound, which is used to produce 3-(1-cyclopropenyl) propanoic acid; and (iii) converting the 3-(1-cyclopropenyl) propanoic acid into its water soluble sodium salt.

* * * * *